United States Patent
Beasley et al.

(10) Patent No.: US 6,827,842 B2
(45) Date of Patent: Dec. 7, 2004

(54) ON-LINE DETERMINATION OF WAX CRYSTALLIZATION TEMPERATURE OF WAXY SOLVENT STREAM

(75) Inventors: Brent England Beasley, Baton Rouge, LA (US); Randall Stephen Lachine, Brights Grove (CA)

(73) Assignee: ExxonMobil Research & Engrg. Co., Annandale, NJ (US)

(*) Notice: Subject to any disclaimer, the term of this patent is extended or adjusted under 35 U.S.C. 154(b) by 489 days.

(21) Appl. No.: 10/000,188

(22) Filed: Oct. 19, 2001

(65) Prior Publication Data

US 2003/0075478 A1 Apr. 24, 2003

(51) Int. Cl.[7] .................... C10G 73/02; C10G 29/20; C10G 73/06; C10G 73/32; G01K 11/06
(52) U.S. Cl. ................... 208/27; 208/28; 208/30; 208/31; 208/33; 208/35; 250/263; 374/160
(58) Field of Search ................ 208/27, 28, 30, 208/31, 33, 35; 250/263; 374/160

(56) References Cited

U.S. PATENT DOCUMENTS

| 4,519,717 A | 5/1985 | Jones et al. ............. 374/17 |
| 4,749,856 A | 6/1988 | Walker et al. ............ 250/227 |
| 4,906,107 A | 3/1990 | Luukkala et al. .......... 374/161 |

FOREIGN PATENT DOCUMENTS

| EP | 0328334 | 8/1989 | ........ G01N/33/28 |
| EP | 0723155 A2 | 7/1996 | ........ G01N/33/28 |

OTHER PUBLICATIONS

Patent Specification—Sixt Frerbrick Kapff, Improvements in or Relating to Pour Point Instruments, Date of Application and filing Complete Spcification: Feb. 4, 1963; Complete Specification Published: Aug. 19, 1964; Patent Specification No. 966,828.

Primary Examiner—Walter D. Griffin
Assistant Examiner—Tam Nguyen
(74) Attorney, Agent, or Firm—Jay Simon; Mark D. Marin

(57) ABSTRACT

A laser beam reflected by wax crystals is used in determining the wax crystallization temperature of a hot dewaxing solvent upstream of solvent chillers. This is automatically achieved by an on-line method from a remote control point, in which a slipstream of solvent is passed through an attached solvent loop into a sample chamber in the loop, without being exposed to ambient conditions. As the sample is cooled, the beam reflections are detected and indicate the wax to crystallization temperature. Corrective measures can then be taken to prevent fouling of the chillers, if need be.

9 Claims, 2 Drawing Sheets

ON-LINE DETERMINATION OF WAX CRYSTALLIZATION TEMPERATURE OF WAXY SOLVENT STREAM

BACKGROUND OF THE DISCLOSURE

1. Field of the Invention

The invention relates to detecting the wax crystallization temperature in a waxy solvent. More particularly, the invention relates to on-line determination of the temperature at which wax crystals form in a dewaxing solvent stream, which comprises passing a solvent sample into a batch chiller into which a laser beam is emitted and cooling the solvent until wax crystal formation reflects the laser beam.

2. Background of the Invention

Higher molecular weight hydrocarbon fractions having an initial boiling point in the 550–650° F. range typically contain wax, irrespective of whether the fraction is derived from natural or synthetic sources. Most wax containing hydrocarbon fractions are derived from naturally occurring sources, such as petroleum, bitumen and the like, but in the future more and more will be derived from synthetic crudes and hydrocarbon fractions produced by processes such as gas conversion, wherein natural gas or a gas comprising primarily methane is converted to a synthesis gas which, in turn, is used to synthesize hydrocarbons. Hydrocarbon fractions boiling in the range of from about 550–650° F. to about 1050° F. are used for lubricating oils for motor vehicles, turbines, machining and the like. In order for a lubricating oil fraction to be useful as a lubricating oil base stock, the wax must first be removed. This is accomplished by either solvent dewaxing or catalytic dewaxing, as is known. Most dewaxing facilities still employ solvent dewaxing, in which a chilled dewaxing solvent is slowly mixed with the lubricating oil fraction and the mixture slowly cooled, under conditions of agitation, down to the desired cloud or pour point temperature. As the mixture is cooled, wax crystals precipitate out, to form a slurry of wax crystals in the cold mixture of solvent and oil. Adding dewaxing solvent to the waxy oil also lowers the viscosity of the mixture. In many cases, a mixture of a wax solvent, such as toluene, and a wax antisolvent, typically comprising ketones such as methyl ethyl ketone and methyl isobutyl ketone, are used to reduce the solubility of the wax in the oil while avoiding oil immiscibility at the wax separation temperature. The wax is typically separated from the mixture of oil and solvent by filtration using rotary vacuum filters. The oily filtrate and wax precipitate are passed to separate fractionaters, to separate and recover the dewaxing solvent from the dewaxed oil and the wax. The hot dewaxing solvent recovered from the fractionaters is passed to indirect heat exchangers referred to as chillers, to lower its temperature sufficient for dewaxing. This temperature is lower than the dewaxing temperature. Wax entrained or carried over with the solvent in the solvent recovery fractionaters often causes fouling in the downstream dewaxing solvent chillers. The fouling comprises wax precipitation and the formation of a layer of wax on the interior heat exchange surfaces of the chillers, which acts as thermal insulation. As a consequence, the temperature of the dewaxing solvent exiting the chillers becomes too high for the downstream dewaxing operation. The chillers must then be taken off-line and cleaned, and this reduces plant capacity. A common way of checking for wax in the chilled solvent is for an operator to take a sample of hot solvent upstream of the chillers, slowly cool it, and visually determine the temperature at which wax crystals form. This is far from perfect. There is no control over the conditions. Taking a sample of hot solvent can be a fire hazard and, further, solvent evaporation while talking the sample can produce an artificially high wax crystallization temperature. In order to make the determination, the sample must be brought to a laboratory or other facility to make the determination. The hot sample is then slowly cooled and the temperature monitored, while watching for wax crystal formation. The temperature at which wax crystals begin to form is taken as the wax crystallization temperature. This method takes too much time to be useful for on-line or real time monitoring. Therefore, it would be advantageous to have a controlled and relatively quick, on-line detection technique capable of detecting the presence of wax in solvent down to a very low ppm. This would enable an operator to take corrective measures before the chillers became fouled and thereby maintain plant capacity.

SUMMARY OF THE INVENTION

The invention relates to a method for determining the temperature at which wax starts to crystallize out of a wax-containing dewaxing solvent upstream of a solvent chiller, without exposing it to the ambient. The method comprises taking a slipstream of the solvent upstream of the chiller and passing it into a sample chamber, into which a laser beam is emitted. The solvent sample containing the dissolved wax is then cooled, preferably under conditions that provide relative motion between it and the beam. The solvent temperature is recorded as it is cooled. As wax crystals start to form in the solvent solution, they scatter and reflect the laser beam striking them, as they pass through it. The reflections are detected and indicate wax crystal formation. The temperature at which the wax crystals begin to form is noted and recorded as the wax crystallization temperature of the sample. The sample chamber, means for passing solvent from the solvent line into the sample chamber, the laser, cooling means and temperature detecting means may be part of a solvent loop attached and adjacent to the dewaxing solvent line. The entire procedure may be accomplished automatically from a remote station. While useful as an on-line method for determining, upstream of a solvent chiller, the wax crystallization temperature of a hot, waxy solvent stream recovered from a wax-solvent and/or oil-solvent fractionater downstream of a rotary vacuum wax filter, the invention is not intended to be so limited. In its broadest sense, the invention comprises a method for determining the temperature at which wax crystals form in a solution of wax dissolved in a solvent (hereinafter "waxy solvent"), wherein the method comprises passing a waxy solvent sample into a batch chiller into which a laser beam is emitted and cooling the solvent until wax crystal formation reflects the laser beam. In another embodiment it comprises determining if wax crystals will form in a solvent at or above a particular temperature, by cooling a solvent free of wax crystals down to the temperature in the presence of a laser beam and noting if wax crystal formation has occurred at or above the temperature, as determined by whether or not the laser beam has been reflected at or above the temperature. If a solvent has wax crystals in it and it is desired to determine the wax crystallization temperature of the solvent, it must first be heated to a temperature high enough to insure complete solution of the wax. In yet another embodiment, the process comprises contacting a waxy oil with cold dewaxing solvent to form a wax precipitate and a dewaxed oil, heating the dewaxed oil and wax and passing them to separate fractionaters to separate the solvent from the wax and oil, passing the hot solvent recovered from the fractionaters to solvent chillers to cool the recovered solvent down to the dewaxing temperature and recycling the cooled solvent back to the solvent dewaxing operation, wherein a sample of the hot solvent being passed to the chillers is cooled to a predetermined temperature in the presence of a laser beam and determining whether or not wax crystals form at or above the predetermined temperature. The predetermined temperature will be somewhat lower than the temperature to which it is desired to cool the solvent in the chillers. If wax crystals do form, then corrective measures are taken upstream to change the conditions in one or more fractionaters, to insure that wax will not form in the solvent in the downstream chillers. When used with a focused, visible light laser beam, this method has determined the formation temperature of wax crystals in a waxy solvent, in which the wax concentration was as low as 12.5 wppm.

DETAILED DESCRIPTION

Figure 1:
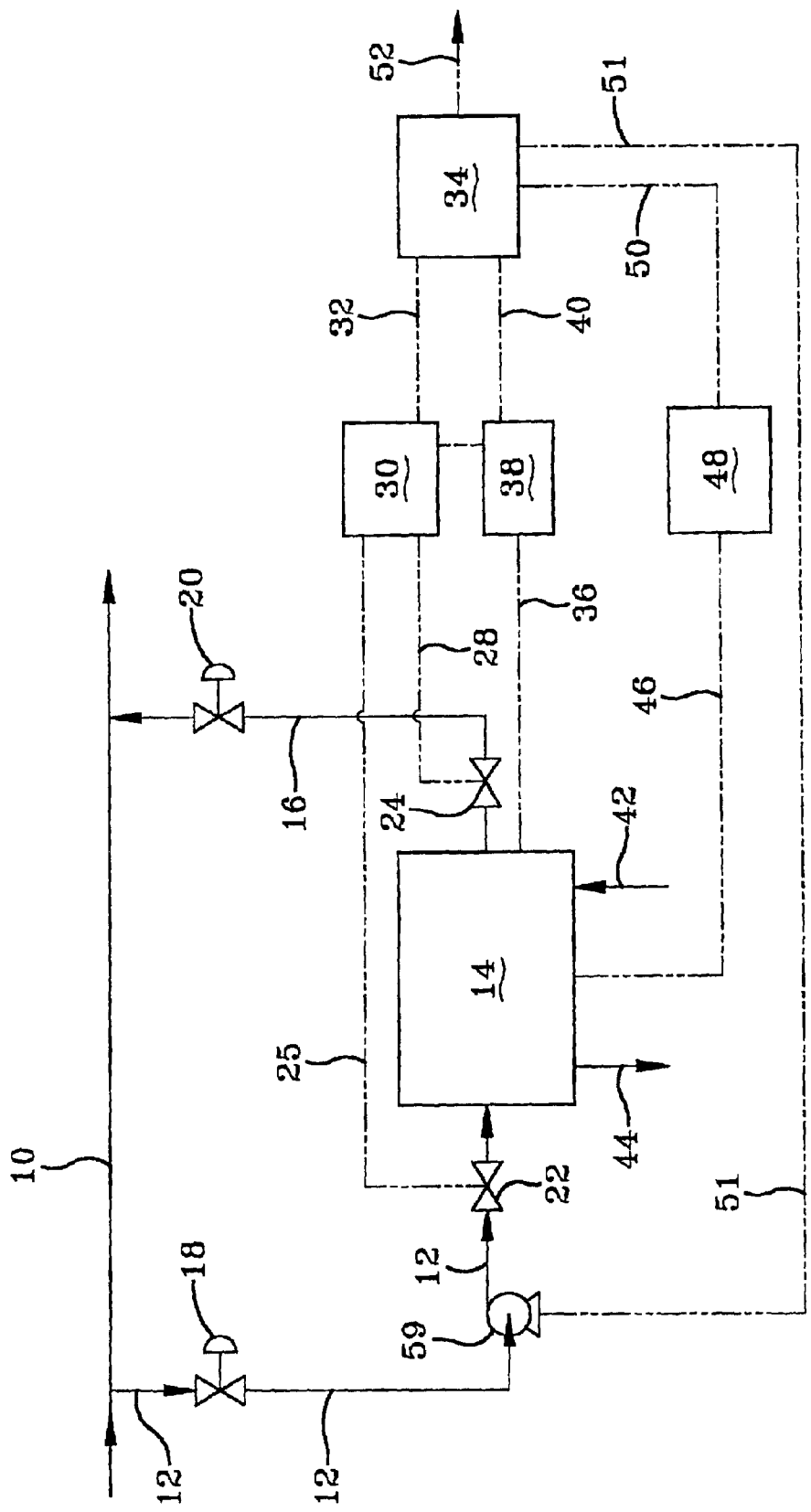
FIG. 1 is a schematic flow diagram of one embodiment of an on-line wax detection method of the invention.

Those skilled in the solvent dewaxing art know that by wax is meant whatever crystallizes out of a hydrocarbon fraction at a given temperature. This is determined by the molecular structure and weight of the molecules crystallizing out of solution. Thus, when referring to the wax content of a particular fraction, one refers to whatever crystallizes out at and above a particular desired temperature. In a solvent dewaxing process, a waxy oil is contacted with cold dewaxing solvent. This crystallizes the wax out of the oil and forms a solvent rich dewaxed oil and a wax precipitate. The solvent may or may not comprise a mixture of a wax prosolvent and a wax antisolvent. The dewaxed oil and the wax are heated and sent to separate fractionaters to recover the dewaxing solvent. The dewaxing solvent recovered from the fractionaters is hot and must therefore be chilled (cooled), before it can be recycled back to the dewaxing operation. This hot, recovered solvent may contain some wax in solution. In the fractionaters, some wax can be carried over into the recovered solvent, due to too high a throughput, too high a temperature, and for several other reasons which are known and need not be discussed. If the wax crystallization temperature of recovered waxy solvent is higher than the temperature to which it will be cooled in the one or more chillers, then wax will crystallize out of solution and form a wax layer on the heat exchange surfaces in the chillers. This acts as thermal insulation. As a consequence, the temperature of the dewaxing solvent exiting the chillers is too high. The chillers must then be shut down, drained and the wax removed. This substantially reduces the capacity of the dewaxing plant. The on-line method of the invention enables facile determination of the wax crystallization temperature of hot, recovered waxy solvent passing to the chillers, so that corrective measures may be taken before the chillers are fowled with wax. By on-line method according to the practice of the invention, is meant that a slipstream of hot, waxy solvent is passed from the solvent line, through a solvent sampling loop and into a sample chamber, without exposing it to ambient or an operator. This is done downstream of the solvent recovery fractionaters and upstream of the solvent chillers. The sampling loop, which contains the chamber, is attached and adjacent to the line. In the sample chamber, the sample is preferably at the same conditions of temperature and pressure existing in the line. As mentioned above and discussed in detail below, all this can be done automatically from a remote control point. Valves in the solvent sample loop are opened to permit a slipstream of the hot solvent in the recovered solvent line to pass into the attached solvent loop, into and through the sample chamber, and back out into the line. The solvent passes through the loop until the solvent in the sample chamber is at the same temperature as that in the line and the valves are closed. The sample in the chamber is slowly cooled under conditions of relative motion between it and the laser beam emitting into it, and its temperature measured as cooling progresses. The temperature at which wax crystal formation reflects the laser beam is the wax crystallization temperature. The laser, chilling means, and also typically the means for providing the relative movement, are then shut off. The sample may then remain in the sample chamber, until it is time for the next determination to be made. This is done periodically to monitor the wax crystallization temperature of the recovered solvent, so that corrective measures may be taken, if necessary to avoid wax crystal formation and deposition in the chillers.

In the process of the invention, the apparatus used comprises a sample chamber, a laser and a method for emitting the laser beam into the sample in the chamber, and means for (i) detecting the reflected beam produced by the presence of a wax crystal passing through it, (ii) measuring the solvent temperature, (iii) producing relative movement between the sample and beam, and (iv) cooling the sample. In addition, the sample chamber may also have (v) means for heating the sample, to insure that the wax is in solution, in the event the sample temperature is below the wax crystallization temperature. When used on-line, these means will preferably all be located adjacent the solvent line upstream of the chiller and isolated from the line by means such as valves in the solvent loop. The sample temperature may be determined by a signal emitting device or means, such as a thermocouple, that produces an electric signal indicative of the temperature and is connected to suitable units for detecting and processing the signal. The relative motion between the laser beam emitted into the solvent sample may be achieved by a simple mixer or impeller in the sample chamber to stir the sample, by moving the laser beam or both. In one embodiment of the invention, a scraping type of mixer in the sample chamber reduces the chances of wax crystals forming on the chamber walls and the laser beam is rotated at a relatively high speed. This is disclosed in detail below. Fiber optic and electrical cables may be used to respectively connect the reflected laser and temperature signals to respective detection and recording units remote from the solvent line and sample chamber. After the wax crystallization temperature is known, the laser and agitation are shut off. The sample chamber isolation valves may then be opened to purge the sample back into the solvent line going to the chiller, or they may remain closed until the next sample is taken.

The laser beam must be scattered or reflected by a small wax crystal, and not adversely effect the process. In general, this eliminates the use of powerful infrared lasers, which would melt the crystals and heat up the waxy solvent. It is preferred that the beam be focused to a relatively small area in the sample solution. This intensifies the radiation striking the wax crystals as they form in the waxy solvent and, concomitantly, also the radiation reflected by the wax crystals. A laser emitting radiation (a laser beam) in the visible portion of the electromagnetic spectrum (visible light) is preferred for a number of reasons. It doesn't heat up the wax crystals or solution, is readily transmitted via fiber optic cable, is easy to focus and the reflected light may be captured and transmitted to a detector and processor, by fiber optic cable. The laser beam may be emitted and focused in the sample through a probe, one end (the tip) of which projects into the sample chamber and terminates in a light transmissive window, through which the visible laser beam is emitted into the sample and focused at a point external of the probe and in the solvent sample in the chamber. The emitted laser beam may also be rotated, to provide all or a portion of the relative movement between wax crystals and the rotational plane of the focused laser beam. A fiber optic cable enables the laser beam to be generated outside of the probe and then passed, via the fiber optic cable, to the probe and then into the sample. In this embodiment, a fiber optic cable is used to capture the reflected beam and pass it to a detecting unit outside of the probe. The laser which emits the laser beam and the detection unit or means (e.g., such as, for example, a light detecting diode) which detects the reflections caused by wax crystals passing through the focal point in the solution, may both be located some distance away from the probe and coupled to it by fiber optic cable. In one embodiment, the laser beam (i.e., light, when the beam is radiation in the visible portion of the electromagnetic spectrum) reflected back up to the probe tip passes through the probe window and into a fiber optic cable. The fiber optic cable passes it out of the probe to light detection and processing circuitry, which records each time a wax crystal passing through the beam's focal point reflects the emitted light back up into the probe and records (counts) it as indicating the presence of a wax crystal. This is processed by a microprocessor, computer or other suitable means, which counts each crystal detected by the laser light and determines the number of crystals detected as a function of time. At the same time, a signal emitting temperature detector means (e.g., a thermocouple) located in the sample emits an electric signal indicative of the temperature and passes this signal to means (e.g., one or more computers and/or microprocessors) for recording it and which preferably also displays the temperature as the sample is cooled. The same or different computer or microprocessor correlates the temperature and light reflections; determines the temperature at which the wax crystals begin to appear, and produces a signal, graph, readout or other indicia indicating the wax crystallization temperature of the solvent sample. If the crystallization temperature is too high, an alarm or other alerting means can indicate the need for immediate attention. This enables an operator to take corrective measures upstream of the solvent chiller, if the temperature at which the wax starts to crystallize is too high or near enough to the desired chill temperature to result in wax precipitation in, and concomitant fouling of, the solvent chiller.

Referring to FIG. 1, there is shown a brief schematic flow diagram of one embodiment of an on-line wax detection method of the invention. Solvent line 10 passes hot dewaxing solvent recovered from one or more fractionaters (not shown), to one or more solvent chillers (not shown). The fractionaters are used to recover the dewaxing solvent from the dewaxed oil and wax resulting from a solvent dewaxing operation. A solvent loop defined by solvent take-off line 12, sample analysis unit 14 and solvent return line 16, is used to pass a slipstream of the hot solvent in line 10 into the solvent sample analysis unit or means 14. Manual isolation valves 18 and 20 are normally open, and are used to isolate sample apparatus or means 14 and automatic valves 22 and 24, for maintenance, repair and replacement. Valves 22 and 24 are automatically actuated to either an open or closed position, by means of a computer 34 and/or an automatic valve sequencer 30. The valves 22 and 24 are pneumatically or electrically connected to the automatic valve sequencer 30 via suitable means, such as fluid conduits or electrical cable indicated by dashed lines 26 and 28. Valve sequencer 30 is in electrical communication, via line 32, with computer 34, which signals the valve sequencer to open or shut valves 22 and 24. A temperature sensing device in apparatus 14 (shown as 72 in FIG. 2) is electrically connected, via line 36, to detector 38. Detector 38 converts an electrical signal emitted by the temperature sensing means to the temperature of the sample in 14 as a function of time during the analyses and passes this information to computer 34. Computer 34 records the temperature as a function of time and also controls the actuation and operation of means (not shown) such as an electric heating blanket and cooling coils, for heating and cooling a sample being analyzed in 14. Heat exchange fluid lines 42 and 44 provide cold or hot heat exchange fluid to cool or heat a sample in 14, via indirect heat exchange using suitable coils or jacket. Heating may also be achieved by an electrical jacket (not shown) around the sample chamber (54 in FIG. 2). A fiber optic cable indicated as 46, communicates optical information to and from a sample analyzing or wax detecting device or unit in the sample chamber (shown as probe 54 in FIG. 2), to field control unit 48. Unit 48 is described in detail below. Unit 48 is in electrical communication with computer 34 via line 50. Computer 34 is at a remote control point and provides a variety of information outputs to an alarm, chart, etc., via line 52, as well as to automatic valve sequencer 30 and means (not shown) for controlling the sample heating and cooling means. In automatic, on-line operation, computer 34 signals valve sequencer 30 to open valve 24 and then valve 22, after which solvent pump 59 is actuated. Pump 59 is controlled by the computer via electrical line 51. This permits any sample in 14 to be purged or flushed out, as a side stream of the hot solvent flowing through line 10 flows through line 12, into the sample chamber in 14 and then out to 10, via line 16. After a few minutes of solvent flow through 14, the computer (i) signals 30 to close valve 24, (ii) shuts off pump 59, and then signals 30 to close valve 22, thereby trapping a sample of solvent in the sample chamber. The computer 34 then signals the cooling means to slowly cool the sample chamber and signals the field unit to actuate the laser beam probe, briefly indicated as probe 56 in FIG. 2, used for the wax crystal is detection. Relative movement between the emitted beam and the sample is initiated before or when the cooling begins, as is explained in detail below. The cooling continues until wax crystals form and reflect the laser beam, which is detected in unit 38. Unit 38 sends this information to the computer. At the same time, the temperature of the sample is being recorded by the computer and correlated with the wax crystal detection. This determines the temperature of the solvent when wax crystallization is detected. In another embodiment, cooling of the sample ceases if wax crystals have not formed within a predetermined temperature range below the temperature to which the hot waxy solvent will be cooled to in the downstream chillers. When the temperature of the solvent reaches the desired low temperature, the computer records the presence or absence of wax crystals at that temperature, which is lower than the temperature to which the hot solvent will be cooled in the one or more chillers downstream. If wax crystals have formed, the computer actuates a signal, alarm, display or other indicia at a control point, so that appropriate means may be taken upstream, to prevent wax build-up in the downstream solvent chillers. The computer also records if wax crystals have not formed, but in this case, does not actuate an alarm. Irrespective of whether or not wax crystals have formed in the solvent sample, after the analysis is completed the computer shuts off the laser, sample cooling and relative movement between the laser beam and sample. The solvent sample is then either warmed up to about the temperature of the solvent going through line 10 or left at whatever temperature was reached. In the later case, when the cycle is repeated, the hot solvent flowing through purges out the previous sample, including any wax present. When the time for talking the next sample is reached, the computer signals valve sequencer 30 to open valves 22 and 24 and actuates pump 59 for a time sufficient to purge out and replace the previous sample. The procedure is automatically repeated at a predetermined cycle sequence.

Figure 2:
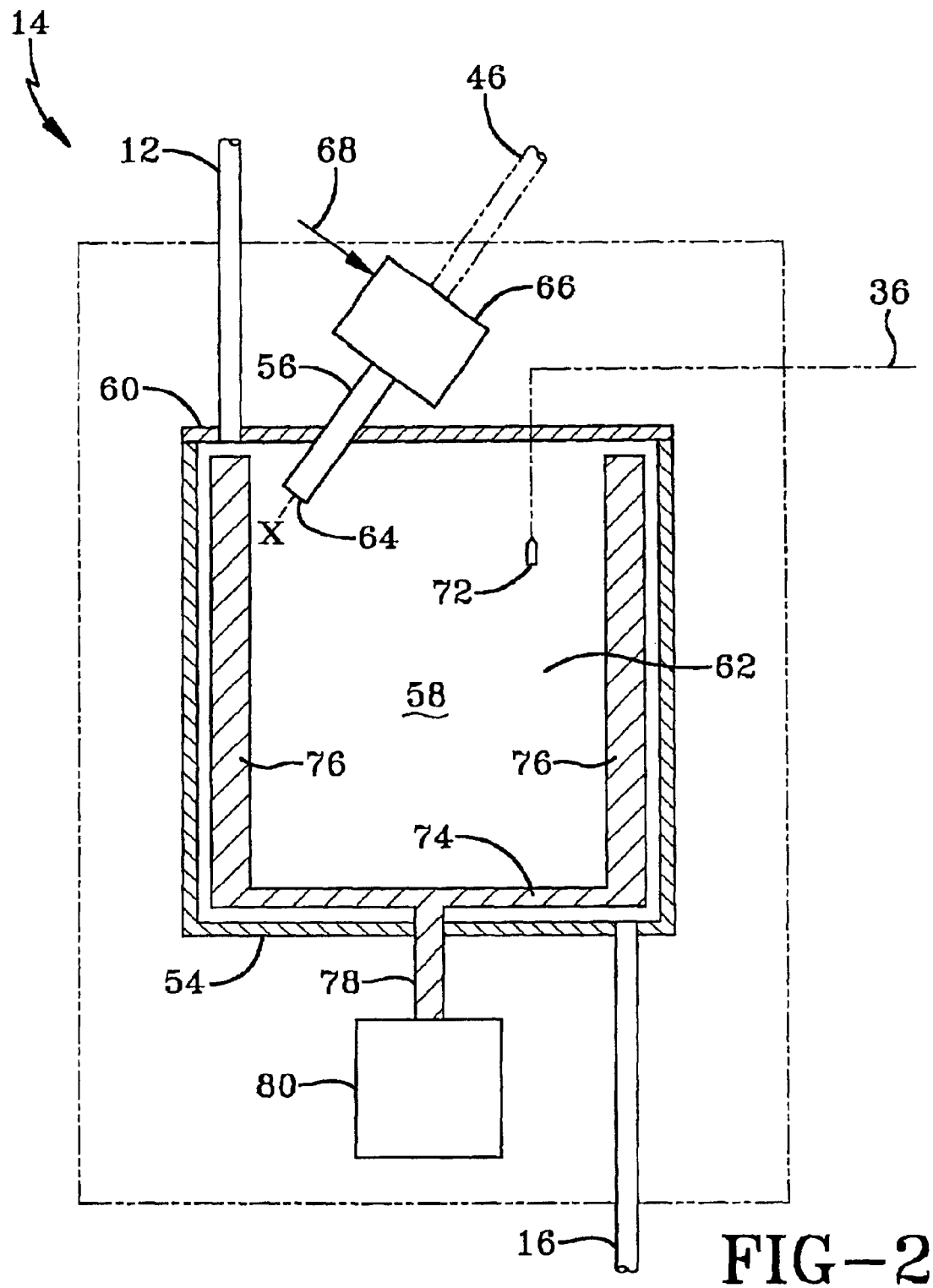
FIG. 2 shows a schematic side view of the wax detection sample chamber and laser probe useful in the embodiment of FIG. 1.

Turning now to FIG. 2, means or apparatus 14 is shown as comprising a stainless steel solvent sample and analysis chamber 54, containing a portion of a laser beam probe 56 and a cavity 58 within, for containing the solvent sample to be analyzed. The laser probe and associated field unit used for this particular illustration is commercially available as an FBRM Series Process Monitor, from Lasentech© in Richmond, Wash. A laser diode in the field unit emits a visible laser beam, which is passed to the probe means via a fiber optic cable. The beam is collimated in the probe. The probe contains a lens by means of which the collimated laser beam can be focused at various distances from the end or tip of the probe. The collimated and focused beam is emitted from the end of the probe, through a sapphire window sealed into its tip. A focusing lens on the exterior of the probe enables the emitted beam to be focused. This particular device also has gas powered motor means associated with the probe, for rotating or spinning the emitted laser beam. The beam is emitted near to the periphery of the cylindrical probe means and not from the center. Thus, when spinning, the focused and emitted beam forms an annular focal plane parallel to the plane of the sapphire window, and perpendicular to the longitudinal axis of the probe. This provides all the relative movement or motion needed. A wax crystal passing through the focal plane reflects and scatters the emitted beam. Part of the beam is reflected back up and through the sapphire window and up into the probe. A beam splitter, such as a prism, directs this reflected beam into a fiber optic cable different from that through which the beam emitted by the laser diode travels. The reflected beam travels through the fiber optic cable to a detector, such as a diode, in the field unit. The diode detector converts each bit of light received into an electrical signal in the form of a pulse. This is amplified and converted to a count. The counts are then sent to a computer, which records the counts as a function of time and provides a suitable output. Such outputs are not limited to this particular apparatus and may comprise one or more of (i) a graph which displays counts as a function of time, (ii) an electrical signal such as a voltage or current whose magnitude is a function of the number of counts (wax particles) detected per unit if time, etc. The electrical signal (s) may be used to sound an alarm, actuate a trouble light, etc., to alert an operator to take appropriate measures upstream of the chiller(s), if necessary, etc.

Turning again to FIG. 2, apparatus 14 comprises a stainless steel sample chamber comprising a cylindrical, stainless steel vessel 54, hermetically sealed at the top with a stainless steel cover 60. The interior 58 of the sample chamber is filled with a liquid solvent sample 62. A cylindrical Lasentech© laser probe 56 is hermetically sealed through cover 60, by means not shown. Solvent lines 12 and 16 are hermetically sealed in the sample chamber top and bottom by compression fittings or other suitable fittings. Not shown is a hollow metal jacket or hollow metal coils surrounding the sample chamber, through which heat exchange fluid is circulated via lines 42 and 44, to cool and heat the solvent sample via indirect heat exchange. Also not shown is an optional heating jacket, which could surround the fluid heat exchange means, for heating the solvent sample. The laser light emitted by the probe is focused into the solvent sample at a finite distance into it, indicated by X. The collimated and focused laser beam is emitted through a light transmissive sapphire window 64 at the bottom or tip of the probe, near to the outer periphery and not the center, as is shown. The light transmissive sapphire window 64 is hermetically sealed in the probe by means not shown and its plane is perpendicular to the longitudinal axis of the probe. The upper portion 66 of the probe contains a gas operated motor means (not shown), for rotating the emitted laser beam in a circle in the solution at a speed of 75 revolutions per second (rps), around the longitudinal axis of the probe. The laser beam is emitted through the tip of the probe in a direction parallel to the probe's longitudinal axis. This forms an annular focal plane in the solvent, parallel to the plane of the sapphire window 64 and perpendicular to the probe's longitudinal axis. Gas line 68 passes the gas for rotating the laser beam into the motor (not shown), in upper portion 66. As wax crystals form, some of them pass through the annular focal plane. As they do so, a portion of the emitted beam is reflected back up through the sapphire window and to a prism or beam splitter (not shown) in the probe, which directs the reflected light into one end of a fiber optic cable in the probe, the other end of which terminates in the field unit 48. Cable 46 passes the reflected light to a light detecting diode (not shown) in 48. There are two fiber optic cables, both of which are adjacent to each other in the same single cable, which is indicated as 46. A laser diode (not shown) in 48 emits the laser light, which is passed through cable 46 and into the probe in which it is collimated to a laser beam, passes through a focusing lens (not shown), and then out of the window 64 and into the solvent sample 62. A thermocouple 72 in the solvent sample is connected to electrical cable 36. A scraping stirrer 74 in the sample vessel comprises at least two, spirally curved scraper blades 76 connected, via a shaft 78 through a suitable seal (not shown), to a motor 80, which turns the scraper. This helps to prevent the build-up of wax on the interior surface of the side walls of the sample vessel and also improves heat transfer. In addition to a scraper, the sample chamber may also contain an impeller (not shown).

EXAMPLES

Five gallons of a solvent consisting of 50/50 volume % MEK/MIBK was made at room temperature and enough wax added to make a 500 wppm mixture of the wax and solvent. All of the wax dissolved in the solvent. The five gallon mixture was then divided into one gallon samples, which were further diluted to make 50, 25 and 12.5 wppm solutions of the wax in the blended ketone dewaxing solvent. These samples were used in the tests below.

Manual Laboratory Method

A small portion of each sample was placed in a test tube, heated to about 60° C. and then slowly cooled, while stirring in an alcohol bath. Wax appearance points were measured visually. The sample was then slowly heated up until the wax crystals disappeared and slowly cooled again until the crystals reappeared. This technique is accurately repeatable and reproducible, if done with care and without cooling so fast as to cause wax crystallization on the interior surface of the sample tube. As the wax crystals start to form, they appear very distinctly as sharp points of reflected light and not as a cloud or haze. The results are set forth in the Table below.

Example

Experiments were conducted with a Lasentec laser probe unit as described above. The probe was hermetically sealed in a sample chamber comprising a stainless steel jacketed vessel having about a 2200 cc liquid capacity and a variable speed mixer located in its center. Cooling was achieved by flowing cold heptane through the jacket and heating was accomplished by an electric blanket around the jacket. The probe tip extended into the vessel, such that the sapphire window at its light emitting tip was about an inch from the mixer. Prior to use the laser probe was calibrated, so that the focal point of the visible laser beam was about 100 microns past the sapphire window and into the solvent solution. The laser light was produced by a laser diode in a field unit external of the probe, with fiber optic cable coupling the diode and probe. The laser light was collimated to a beam in the probe, which was then emitted through the sapphire window, with its focal point in the solvent. The solvent solution was then slowly cooled. As the wax crystals began to appear in the cold solvent, some of the focused laser beam was reflected off the crystals, back into the probe, and then through the fiber optic cable to a light detection means in the field unit.

Each run started with the solvent solution at a temperature between 70–80° C., to insure that all the wax was dissolved, and the temperature delta across the sample chamber wall was maintained at less than 5° C. during the cooling. The speed of the variable speed solvent mixer in the sample vessel was adjusted to achieve a stable baseline of the wax particle counts, during the wax crystallization temperature measurements. The cooling rate varied, depending on the wax concentration in the sample, with higher concentrations requiring slower cooling rates, to prevent wax crystallization on the vessel walls. Less than about 3° C./min during each run was typical. Relative movement between the emitted laser light and the wax particles in the solution was achieved by rotating the tip of the probe and, concomitantly, the emitted focused laser light. The probe tip was rotated at a speed of 75 rps in the waxy solvent as it was cooled. This produced an annular plane of the focused laser light in the solution, parallel to the plane of the sapphire window at the tip of the probe. This plane was perpendicular to the longitudinal axis of the probe.

A portion of the laser light reflected off the wax crystals passed back through the sapphire window and into the probe, from where it was passed back into the control unit by a fiber optic cable and detected by a photodiode. The detected light was converted into electrical pulses, which were classified by time, and the number of pulses per unit of time recorded as counts. These counts ware recorded cumulatively and accumulated in a computer, which produced a curve of the number of counts (wax crystals) as a function of time. At the same time, the temperature of the sample was measured by a thermocouple electrically connected to the computer, which combined the temperature information with the counts, so that the counts as a function of temperature was known. From this, the temperature at which wax crystals began to form in solution was determined. In a refinery, this is easily calibrated and converted to, for example, a visual and/or audio alarm and/or a graphic display or other indicia, enabling an operator in a remote control room to take the necessary action (e.g., reduce the operating temperature or solvent feed rate into the one or more fractionaters).

Results

The results of both this example and the Manual Laboratory Method are shown in the Table below. Not only was the laser beam method able to detect wax crystals as they began to crystallize out of the solution in which the wax concentration as low as 12.5 ppm, there was also overall very good agreement between the laser method and the Manual Laboratory Method.

| | Wax crystallization temp. | |
|---|---|---|
| PPM of wax in solvent | Laser probe method | Manual method |
| 50 | −9° C. | −7° C. |
| 25 | −14° C. | −12° C. |
| 12.5 | −17° C. | −17° C. |

What is claimed is:

1. A solvent dewaxing process comprises:
   (a) contacting a waxy oil with cold dewaxing solvent to form a dewaxed oil and wax, both of which contain said dewaxing solvent;
   (b) heating said solvent containing dewaxed oil and wax and then passing same to separate solvent recovery fractionaters to separate and recover said solvent;
   (c) passing said hot recovered dewaxing solvent produced in (b) into a solvent line that passes it to solvent chillers downstream of said fractionaters and wherein said hot solvent is cooled back down to the cold dewaxing temperature in said chillers and recycled back to solvent dewax more waxy oil;
   (d) passing a slipstream of said hot recovered solvent from said line upstream of said chillers into a solvent loop containing a sample chamber and into said chamber without exposing said sample to the ambient, wherein said chamber contains wax crystal detecting means comprising a laser beam that is reflected by wax crystals focused at a point in said sample in said chamber, wherein wax crystals forming in said sample that pass through said focal point reflect said beam, and wherein said reflections are detected and recorded as indicating the presence of said wax crystals in said sample, and
   (e) cooling said sample in said chamber under conditions of relative motion between said beam and sample down to a predetermined temperature or until wax crystals form and are detected, and recording the temperature at which they form under conditions that provide relative movement between said beam and sample.

2. A dewaxing process according to claim 1 wherein the temperature at which said wax crystals form is automatically recorded an wherein if the temperature at which said wax crystals form is too high, one or more operators are alerted and corrective measures are taken upstream of said chillers to prevent them from being fouled with wax.

3. A dewaxing process according to claim 2 wherein said laser beam comprises visible light radiation.

4. A dewaxing process according to claim 3 wherein said solvent loop is attached and adjacent to said solvent line.

5. A dewaxing process according to claim 4 wherein said steps (d) and (e) are accomplished by remote control at a control point remote of said solvent loop and chamber.

6. A dewaxing process according to claim 5 wherein said steps (d) and (e) are automatically repeated at predetermined intervals.

7. A dewaxing process according to claim 6 wherein said solvent sample is passed back into said solvent line via said loop after steps (d) and (e) have been achieved.

8. A dewaxing process according to claim 7 wherein said sample in said chamber is at the same conditions of temperature and pressure as said hot solvent in said line before it is cooled.

9. A dewaxing process according to claim 8 wherein said dewaxed oil comprises a lubricating oil fraction.

* * * * *